United States Patent [19]

Schiwiora et al.

[11] Patent Number: 4,767,329
[45] Date of Patent: Aug. 30, 1988

[54] T-ATTACHMENT FOR THE DETACHABLE FASTENING OF DENTAL PROSTHESES

[75] Inventors: Harry Schiwiora, Pforzheim; Willi Ahr, Birkenfeld; Alfred Schart, Olbronn/Dürrn, all of Fed. Rep. of Germany

[73] Assignee: Degussa Aktiengesellschaft, Frankfurt am Main, Fed. Rep. of Germany

[21] Appl. No.: 33,702

[22] Filed: Apr. 3, 1987

[30] Foreign Application Priority Data

Apr. 4, 1986 [DE] Fed. Rep. of Germany ....... 3611322

[51] Int. Cl.$^4$ .......................................... A61C 13/225
[52] U.S. Cl. ................................... 433/181; 433/182
[58] Field of Search ................ 433/182, 180, 181, 183

[56] References Cited

U.S. PATENT DOCUMENTS

| 2,271,796 | 2/1942 | Eckman | 433/182 |
| 3,117,377 | 1/1964 | Poveromo | 433/182 |
| 4,196,516 | 4/1980 | Poveromo | 433/182 |
| 4,474,499 | 10/1984 | Pedrazzini | 433/182 |

FOREIGN PATENT DOCUMENTS 2217088 10/1972 Fed. Rep. of Germany ...... 433/181

Primary Examiner—John J. Wilson
Attorney, Agent, or Firm—Cushman, Darby & Cushman

[57] ABSTRACT

A T-attachment for the detachable fastening of dental prostheses and bridges to the residual denture which is still elastic after activation and which makes possible an even friction. The T-attachment consists of a matrix and a patrix. The patrix is provided with a continuous slot and has a longitudinal beam. An activation part is attached to the longitudinal beam, and also is provided with a slot. The slot in the activation part is open adjacent the longitudinal beam of the patrix, but has a closed slot end within the activation part. Activation is achieved by means of a conical screw which is inserted parallel to the slot end, within the activation part, the cone of the screw being located in the shaft area of the screw.

5 Claims, 2 Drawing Sheets

Fig. 5.
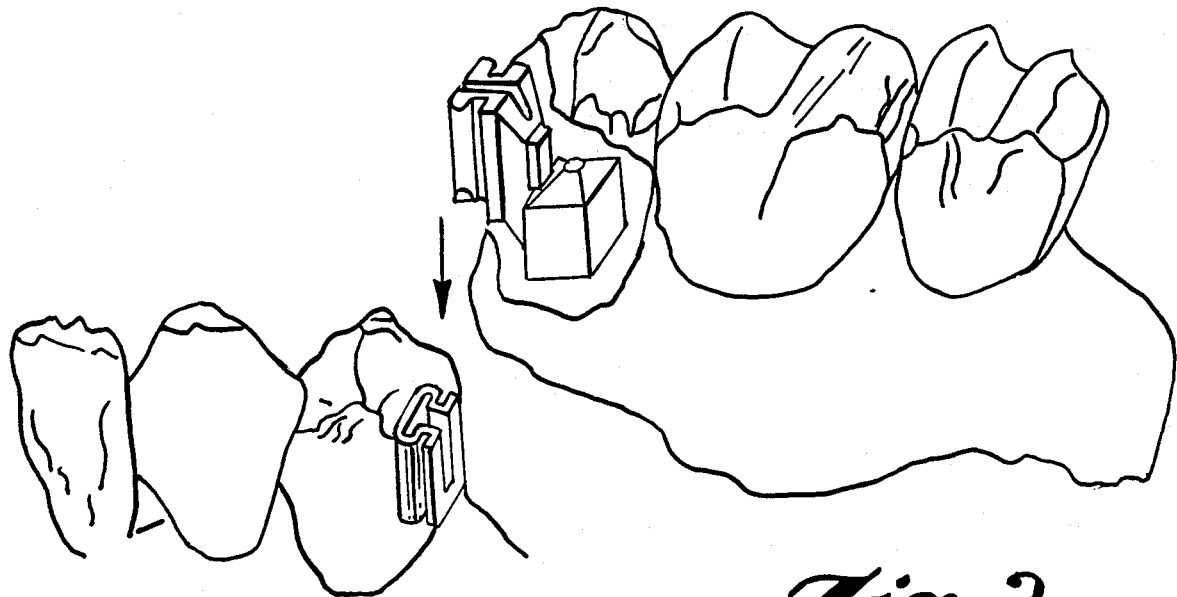
Fig. 2.
Fig. 1.
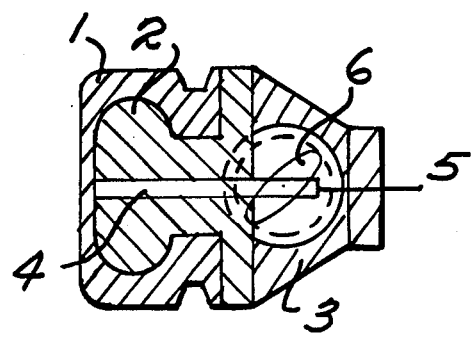
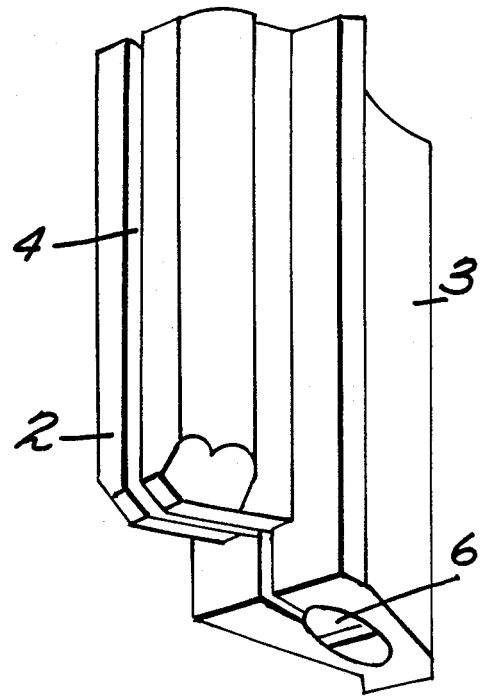

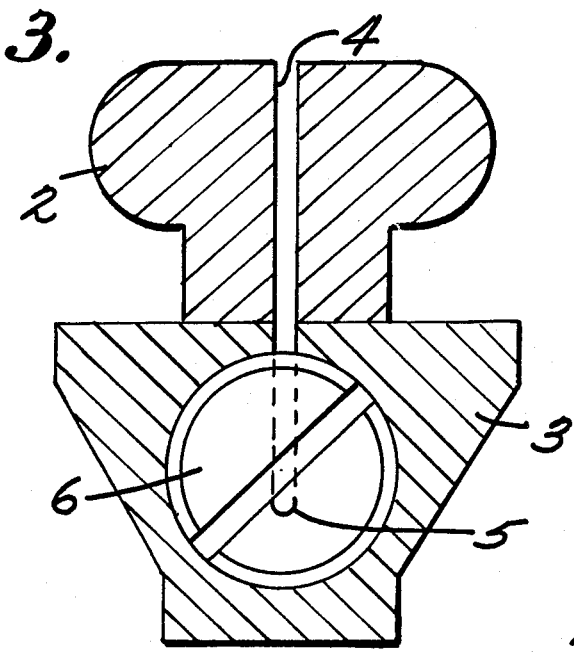
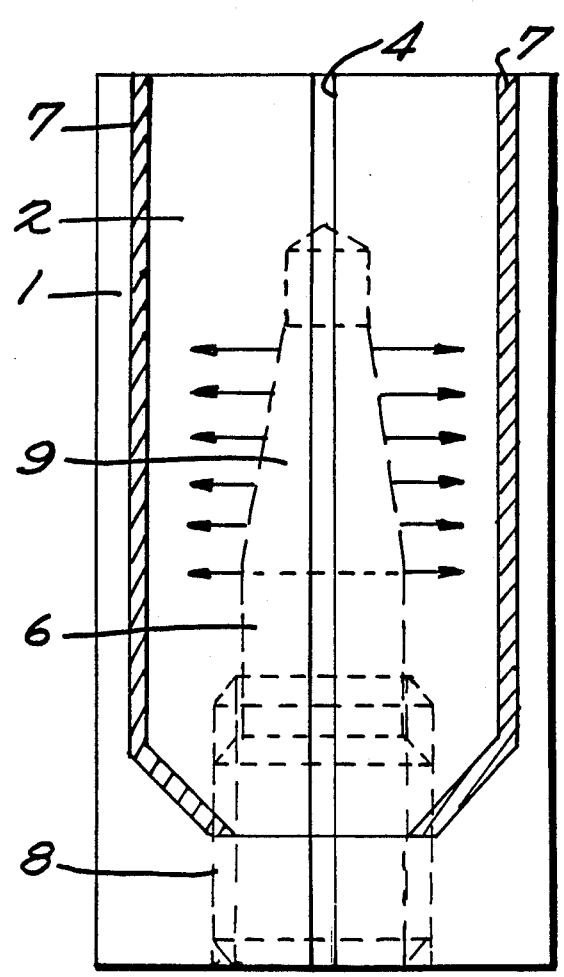

T-ATTACHMENT FOR THE DETACHABLE FASTENING OF DENTAL PROSTHESES

The present invention relates to a T-attachmnt for the detachable fastening of dental prostheses and bridges to natural teeth. The T-attachment according to the invention includes a female part or matrix and a patrix or male part. The male part is provided with a continuous slot which can be activated by a conical screw, to tighten it in the matrix. An activation part is attached to the longitudinal beam of the patrix and it also is provided with a slot.

BACKGROUND OF THE INVENTION

Many types of T-attachments are used in dentistry in order to fasten prostheses and removable bridges. Such devices are illustrated for example in U.S. Pat. No. 4,196,516 and European Patent Specification No. 0,085,781. They consist of a male part of patrix and a female part or matrix. The matrix surrounds the patrix to a large extent, in order to assure a firm seating of the patrix in the matrix. Usually, the patrix is slotted from the occlusal or the gingival side. The lamellae formed by the slot are bent up by widening the slot with special tools. This feature imparts an additional friction to the patrix so that the patrix is seated even more firmly in the matrix. This process is designated as "activation".

The coupling area between the residual teeth and the removable prosthesis is an area which is particularly heavily stressed in the mouth. Especially during movements about the transverse axis, the slot in the patrix is gradually compressed, regardless of whether the slot is located in the occlusal or the gingival area of the patrix. Since this causes the seating of the patrix in the matrix to become loose, these T-attachments must be reactivated at frequent intervals to assure that the prosthesis is firmly seated in the mouth.

T-attachments are also used in which the patrix is provided with a continuous slot and the patrix halves are held together by a partially slotted longitudinal beam of the patrix. The slot is spread by means of a screw provided with a conical head. This screw is turned sagittally into the front surface of the slotted patrix. However, the spread-apart patrix body is rigid after activation, since the elastic patrix halves are supported on the screw head. In addition, the patrix parts are mechanically weakened by the position of the screw on the front surface of the patrix. The correct point of friction is difficult to find in rigidly fixed parts, so that, in the case of an over-activation, the patrix can easily be jammed in the matrix. In case there is insufficient activation, the friction is insufficient.

SUMMARY OF THE INVENTION

The object of the present invention is to provide a T-attachment for the detachable fastening of dental prostheses and bridges to the residual denture, consisting of a matrix and an patrix which is provided with a continuous slot, and which can be activated by a conical screw. an activation part is attached to the longitudinal beam of the patrix, and the activation part is also provided with a slot, aligned with the slot in the patrix. The patrix remains elastic even after activation, thus making possible an individually adjustable, even friction between the patrix and the matrix.

The invention achieves this objective as follows: Activation is achieved with a screw which has a conical portion in the shaft area of the screw. The screw is introduced into the slot within the activation part, parallel to the slot end. It is preferable if the screw can be introduced into the slot close to the slot end.

It has proven to be advantageous if the screw cone has an angle of 5 to 35 degrees, especially an angle of 15 to 25 degrees.

It is also advantageous if the cone on the screw shaft is located in the central area of the activation part, in relation to the total height of the activation part or of the patrix, when the screw is screwed in.

The T-attachment of the invention has the advantage that the activation system is located outside of the actual patrix. This prevents the patrix from being weakened mechanically by a screw bore and the elasticity of the patrix halves is preserved. The forces which arise in the differnet axes during mastication are therefore absorbed in an elastically dampening manner and can not deform the patrix parts resting in the matrix.

As a result of the preferred position of the cone in the central area of the total height of the patrix, the two die halves are spread in parallel. This achieves an even friction over the entire attachment surface, the degree of which can be set individually.

The matrix can be cast, since deformations of the matrix produced during casting are compensated by the elastic shanks of the patrix. Also, it is more economical to cast the matrix than to solder it.

The patrix is preferably anchored to the prosthesis by a screw device so that the patrix can be replaced and does not have to be subjected to any thermal treatment during mounting, which could diminish its rigidity.

Since the patrix can be replaced, it is possible to use economical, very rigid alloys which permit a more graceful shaping of the patrix.

BRIEF DESCRIPTION OF FIGURES OF DRAWING

FIGS. 1 to 6 show a representative embodiment of the T-attachment of the invention schematically. More specifically, FIG. 1 shows a cross-section;

FIG. 2 shows a perspective view of a patrix;

FIG. 3 shows a section through another patrix form;

FIG. 4 is a longitudinal section through a conical screw used in the invention; and FIG. 5 is a view which illustrates insertion of the attachment in the mouth.

FIG. 6 shows a perspective view of a conical screw.

DETAILED DESCRIPTION OF PREFERRED EMBODIMENT

The T-attachment illustrated in the drawings consists of a matrix (1) and an patrix (2), to whose longitudinal beam an activation part (3) is attached. The patrix (2) is provided with a continuous slot (4) which divides the patrix (2) into two halves and which extends vertically and in the longitudinal direction. The slot (4) continues approximately until the middle of the activation part (3), so that two elastic shanks are created. A conical screw (6) is screwed into the slot (4) parallel to the slot end (5) and preferably in the immediate area of the slot end (5), which screw presses the patrix halves apart and effects the desired friction between patrix (2) and matrix (1). The expansion range (7) is indicated in FIG. 4.

The screw (6) advantageously comprises a threaded screw head (8), while the conical portion (9) is located on the screw shaft and is preferably located in the central area of the activation part (3) or of the patrix (2), in relation to the total height of the patrix (2).

What is claimed is:

1. A T-attachment for the detachable fastening of dental prostheses and bridges to the residual denture, comprising a matrix (1), a patrix (2) received within said matrix and an activation part (3) attached to the side of the patrix externally of said matrix, the patrix having a generally T-shaped horizontal cross section and having a continuous vertical slot (4) which divides the patrix into two portions, each having a generally L-shaped horizontal cross section, the slot (4) extending into, but ending in the activation part (3) to form a vertical slot end (5), and a screw (6) having a conical portion (9), introduced vertically into the slot (4) within the activation part (3), parallel to the slot end (5), the conical portion (9) of the screw being located in the shaft area of the screw (6), said screw activating said patrix into frictional engagement within said matrix.

2. A T-attachment according to claim 1, in which the screw (6) is introduced into the slot (4) in the vicinity of the slot end (5).

3. A T-attachment according to claim 1 or claim 2, in which the conical portion (9) of screw (6) exhibits an angle of 5 to 35 degrees.

4. A T-attachment according to claim 1 or claim 2, in which the conical portion (9) of the screw (6) exhibits an angle of 15 to 25 degrees.

5. A T-attachment according to claim 1 or claim 2, in which the cone (9) is located in the central area of the activation part (3), in relation to the total height of the activation part.

* * * * *